(12) United States Patent
Kawashima

(10) Patent No.: US 6,766,540 B2
(45) Date of Patent: Jul. 27, 2004

(54) FACE MASK

(75) Inventor: Haruo Kawashima, Tokyo (JP)

(73) Assignee: Tabata Co., Ltd., Tokyo (JP)

( * ) Notice: Subject to any disclaimer, the term of this patent is extended or adjusted under 35 U.S.C. 154(b) by 0 days.

(21) Appl. No.: 10/384,527

(22) Filed: Mar. 11, 2003

(65) Prior Publication Data

US 2003/0172445 A1 Sep. 18, 2003

(30) Foreign Application Priority Data

Mar. 12, 2002 (JP) ........................................ 2002-067603

(51) Int. Cl.[7] .............................................. A61F 9/02
(52) U.S. Cl. ................................ 2/452; 2/428; 24/197; 24/265 BC; 24/163 R
(58) Field of Search ........................... 2/452, 428, 426, 2/438; 351/43, 156; 24/197, 198, 200, 163 R, 265 BC, 265 EC, 265 AL, 3.3

(56) References Cited

U.S. PATENT DOCUMENTS

| | | | | |
|---|---|---|---|---|
| 3,879,804 A | * | 4/1975 | Lawrence | 24/3.3 |
| 5,329,643 A | * | 7/1994 | Sato | 2/428 |
| 5,959,714 A | * | 9/1999 | Chou | 351/43 |
| 6,070,272 A | * | 6/2000 | Chiang | 2/442 |
| 6,105,177 A | * | 8/2000 | Paulson et al. | 2/431 |
| 6,350,030 B2 | * | 2/2002 | Fujima | 351/43 |
| 6,351,874 B1 | * | 3/2002 | Suggs | 24/265 BC |
| 6,477,717 B1 | * | 11/2002 | Winefordner et al. | 2/428 |
| 6,505,353 B2 | * | 1/2003 | Sung | 2/428 |
| 6,550,110 B1 | * | 4/2003 | Kawashima et al. | 24/265 BC |

* cited by examiner

*Primary Examiner*—Rodney M. Lindsey
(74) *Attorney, Agent, or Firm*—Clark & Brody

(57) ABSTRACT

A face mask has a lens frame, buckles mounted on transversely opposite extremities of the lens frame, a headband having its longitudinally opposite end portions adjustably held by the respective buckles and a pair of band guides which the headband passes through. The headband is provided on its longitudinally opposite end portions with a plurality of engagement teeth. Each of the band guides has a first guide opening and a second guide opening. The first guide opening is formed with a first guide area and a second guide areas. The first guide area is adapted to guide zones of the end portion extending along its transversely opposite side edges 8 and the second guide area is adapted to guide the engagement teeth. The second guide opening has a height corresponding to or slightly larger than a thickness t of the end portion.

2 Claims, 3 Drawing Sheets

FACE MASK

BACKGROUND OF THE INVENTION

This invention relates to a face mask used for diving or the other purposes.

Conventional face masks have a lens frame, a pair of buckles mounted on transversely opposite ends of the lens frame and a headband turning around the respective buckles so that a peripheral length of the headband may be adjusted. The headband made of a suitable flexible elastic material such as urethane rubber wherein band guides are used so that the end portions may be stabilized and prevented from obstructing a mask wearer s movement. The headband is formed with a plurality of engagement teeth arranged intermittently in a longitudinal direction of the headband so that any one of the engagement teeth may be engaged with the buckles to adjust a peripheral length of the headband.

In the conventional face masks used for diving or the other purposes as mentioned above, each of the band guides is formed with a first guide opening through which the end portion of the head band is guided from the backside toward the front of the face mask and a second guide opening through which the same end portion is guided from the front toward the backside of the headband after this end portion has been turned around the associated buckle. The guide openings have cross-sections dimensioned to be considerably larger than a cross-section of the headband so that the end portion of the headband may be easily guided through these guide openings. When it is desired to adjust the peripheral length of the headband, the most suitable one of the engagement teeth is brought in engagement with the associated buckle as the headband is moved through the first guide opening of the band guide in a back-and-forth direction of the headband. However, the headband made of silicone rubber or the like is so flexible that the headband may be often unstable within the first guide opening during adjustment of the headband's peripheral length. Specifically, the engagement tooth may be forcibly brought in contact with a peripheral edge of the first guide opening and thereby obstruct smooth movement of the headband in the back-and-forth direction.

SUMMARY OF THE INVENTION

It is an object of this invention to improve a face mask used for diving or the other purposes so that the headband can be smoothly moved through the band guides in the back-and-forth direction to adjust the peripheral length of the headband.

According to this invention, there is provided a face mask comprising a lens frame, buckles mounted on transversely opposite extremities of the lens frame, a headband having longitudinally opposite end portions respectively turning around the buckles so that a peripheral length of the headband is adjusted, and band guides carried by the headband so as to guide the headband passing therethrough.

This invention further comprises the headband made of a flexible elastic plastic and the longitudinally opposite end portions thereof respectively having transversely opposite side edges extending in parallel to a longitudinal direction of the headband, a width of the headband between the side edges as well as a thickness of the headband measured along the side edges being substantially uniform, the end portions being formed on transversely middle zones of respective inner surfaces thereof destined to come in contact with a mask wearer's head with a plurality of engagement teeth arranged intermittently in a longitudinal direction of the end portions each projecting from one of the inner surfaces and having a front surface gently sloping toward a pointed distal end of one of the end portions in the longitudinal direction and a rear surface abruptly sloping in an opposite direction. Each of the buckles acts upon any one of the engagement teeth under a spring-biasing effect to enable the peripheral length of the headband to be adjusted. Each of the band guides has a first guide opening through which the associated one of the end portions is guided from a backside toward a front of the face mask and a second guide opening through which the end portion is guided from the front toward the backside of the face mask after the end portion has been turned around the associated one of the buckles. Both the first guide opening and the second guide opening have a width corresponding to a width of the headband and a height corresponding to a thickness of the headband. The first guide opening is formed with a first guide area adapted to guide transversely opposite lateral zones the end portion extending along its respective side edges and a second guide area being contiguous to the first guide area and allowing the engagement teeth. The first guide area has a width and a height dimensioned to allow the lateral zones extending along the side edges of the end portion to be slidably moved as the end portion is moved in a back-and-forth direction of the face mask. The second guide area has a width and a height respectively dimensioned to be larger than a width and a height of the engagement teeth so that the engagement teeth may freely pass the guide area. The second guide opening has a height substantially same as or slightly larger than the thickness of the end portion and smaller than a sum of the thickness of the end portion and the height of the engagement teeth so as to prevent the end portion passing therethrough from unintentionally moving and simultaneously to prevent the end portion from coming off from the associated one of the engagement teeth.

This invention includes the following embodiments A plurality of the engagement teeth are provided substantially at a regular spacing in the longitudinal direction of the headband and a dimension of the second guide opening in the longitudinal direction corresponds to the regular spacing.

DETAILED DESCRIPTION OF THE PREFERRED EMBODIMENTS

Details of a face mask according to this invention will be more fully understood from the description given hereunder in reference to the accompanying drawings.

Figure 1:
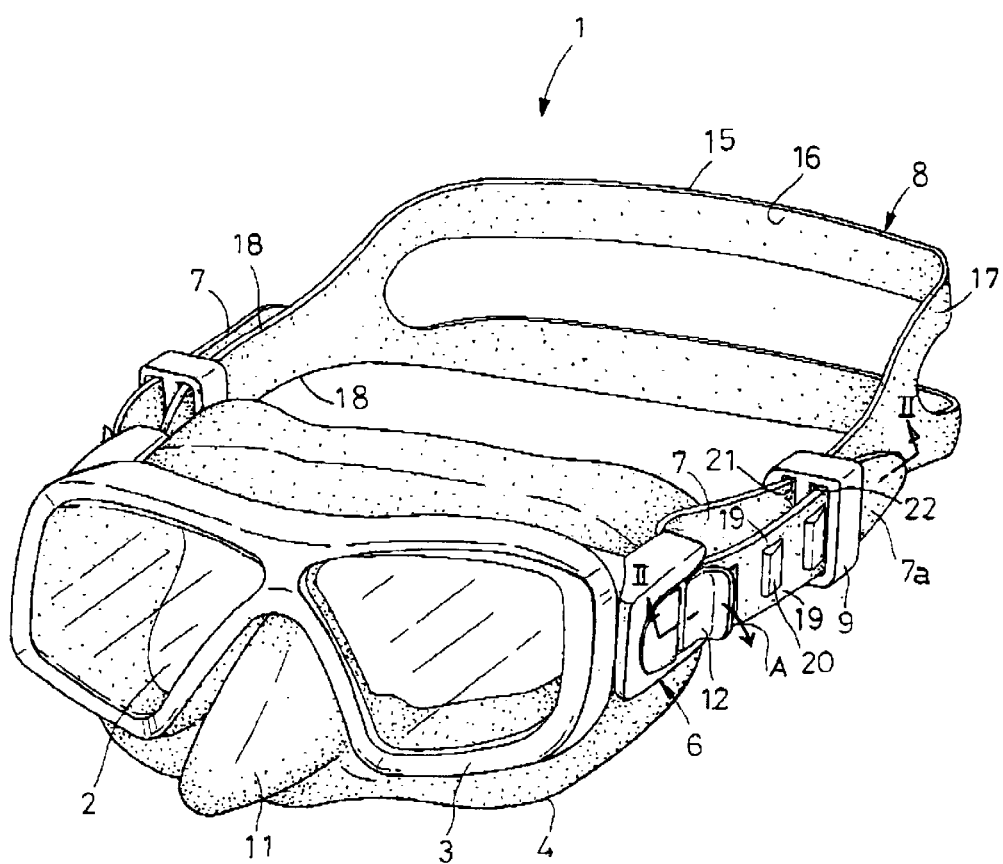
FIG. 1 is a perspective view of a face mask.

A face mask 1 shown in FIG. 1 in a perspective view comprises a lens frame 3 holding therein a pair of lenses 2, a rubber skirt 4 extending rearward from the lens frame 3, buckles 6 provided on transversely opposite extremities of the lens frame 3 and a headband 8 having its longitudinally opposite end portions 7 adjustably held by the respective buckles 6 and a pair of band guides 9 which the headband 8 passes through. The lenses 2 are made of inorganic or organic glass and the lens frame 3 is made of rigid plastics The rubber skirt 4 includes a nose cover 11 projecting forward and entirely made of flexible elastic material such as silicone rubber. The buckles 6 and the band guides 9 are made of rigid plastics and, like the skirt 4, the headband 8 is made of flexible elastic material such as silicone rubber.

Each of the buckles 6 includes a spring-loaded arm 12 normally biased to be pressed against the associated one of the longitudinally opposite end portions 7 of the headband 8 turning around this associated buckle 6. The arm 12 may be moved against a biasing effect of the spring in a direction indicated by an arrow A to bring the arm 12 off from the end portion 7 and thereby to move the end portion 7 in a back-and-forth direction of the face mask 1. In this way, a peripheral length of the headband 8 can be adjusted.

The headband 8 is composed of an intermediate section 15 lying behind a head of a wearer of the face mask 1 and a pair of the end portions 7 extending forward from the intermediate section 15 and has an inner surface 16 destined to come in contact with the head and an outer surface 17 opposed to the inner surface 16. Each of the end portions 7 has transversely opposite side edges 18, i.e., upper and lower side edges as viewed in FIG. 1, extending in parallel to each other except a pointed distal end 7a. A width W of the headband 8 between the side edges 18, 18 as well as a thickness t of the headband 8 along these side edges 18, 18 (See FIG. 3 also) may be uniformly dimensioned. It should be noted that the end portion 7 is formed in a transversely middle zone of its inner surface 16 with a plurality of engagement teeth 20 arranged intermittently in the longitudinal direction of the end portion 7 each projecting from the inner surface 16, each of the engagement teeth 20 is relatively long in the transverse direction.

Each of the band guides 9 has a first guide opening 21 and a second guide opening 22. The end portion 7 of the headband 8 passes through the first guide opening 21 from the backside toward the front of the face mask 1 and through the second guide opening 22 from the front to the backside.

Figure 2:
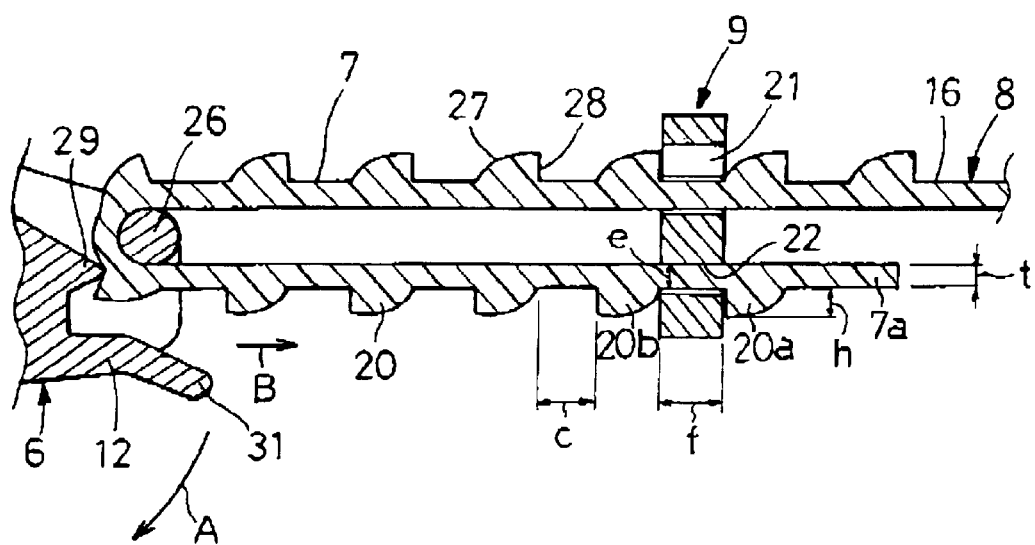
FIG. 2 is a sectional view taken along a line II—II in FIG. 1.

FIG. 2 is a sectional view taken along a line II—II in FIG. 1. The respective end portions 7 of the headband 8 extend from the backside toward the front of the face mask 1 (from the right toward the left as viewed in FIG. 3) and then turn around a supporting bars 26 of the respective buckles 6 with the respective pointed distal ends 7a extending rearward. A plurality of the engagement teeth 20 formed on the inner surfaces 16 of the respective end portions 7 are arranged at a regular spacing c in the longitudinal direction of the headband 8. On the section of the end portion 7 extending from the backside toward the front of the face mask 1, each of the engagement teeth 20 has a front surface 27 gently sloped in the back-and-forth direction and a rear surface 28 abruptly sloped in the back-and-forth direction. The rear surface 28 is illustrated to extend substantially at rights with respect to the end portion 7. On the section of the end portion 7 just turning around the supporting bar 26, a stopper 29 projecting from the arm 12 of the buckle 6 is normally spring-biased to come in engagement with a root of the rear surface 28 of the individual engagement tooth 20 The front surface 27 of this ,engagement tooth 20 depresses the stopper 29 of the arm 12 from above so as to rotate the arm 12 in the direction indicated by the arrow A as the end portion 7 is pulled in a direction indicated by an arrow B against the spring-biasing force. Thereupon the end portion 7 moves in the direction of the arrow B and the peripheral length of the headband 8 is correspondingly shortened. Pulling the end portion 7 in the direction opposite to the direction of the arrow B causes the rear surface 28 of the engagement tooth 20 to be pressed against the stopper 29 of the arm 12 from below as viewed in FIG. 2 and thereby causes the stopper 29 to be forcibly pressed against the end portion 7 of the headband 8. In this way, the stopper 29 effectively functions to prevent the end portion 7 from moving in the direction opposite to the direction of the arrow B and thereby to prevent the peripheral length of the headband 8 from being unintentionally elongated. On the contrary, rotating the arm 12 with a finger-grip 31 being held in the direction of the arrow A causes the stopper 29 of the arm 12 to come off from the end portion 7 and thereby allows the end portion 7 to be moved in the direction opposite to the direction of the arrow B so as to elongate the peripheral length of the headband 8.

Each of the band guides 9 allows the end portion 7 of the headband 8 to move through the first guide opening 21 in the direction of the arrow B as well as in the direction opposite to this direction of the arrow B. Unlike the first guide opening 21, the second guide opening 22 is dimensioned to have a height e substantially corresponding to the thickness t of the end portion 7 or slightly larger than this thickness t but substantially smaller than a sum of the thickness t and a height h of the individual engagement tooth 20. Furthermore, the second guide opening 22 has a dimension f, as measured in the back-and-forth direction, substantially corresponding to the spacing c of each pair of the adjacent engagement teeth 20, 20. Consequently, it is difficult for the engagement tooth 20, 20 being adjacent to each other with the second guide opening 22 therebetween to pass the second guide opening 22. The band guide 9 illustrated as a typical embodiment is normally retained between two engagement teeth 20a, 20b lying most close to the pointed distal end 7a of the headband 8 and therefore the band guide 9 can not unintentionally fall off from the pointed distal end 7a of the headband 8. These engagement teeth 20a, 20b will be able to pass through the second guide opening 22 as these engagement teeth 20a, 20b are forcibly depressed so that the height h thereof may be sufficiently reduced.

Figure 3:
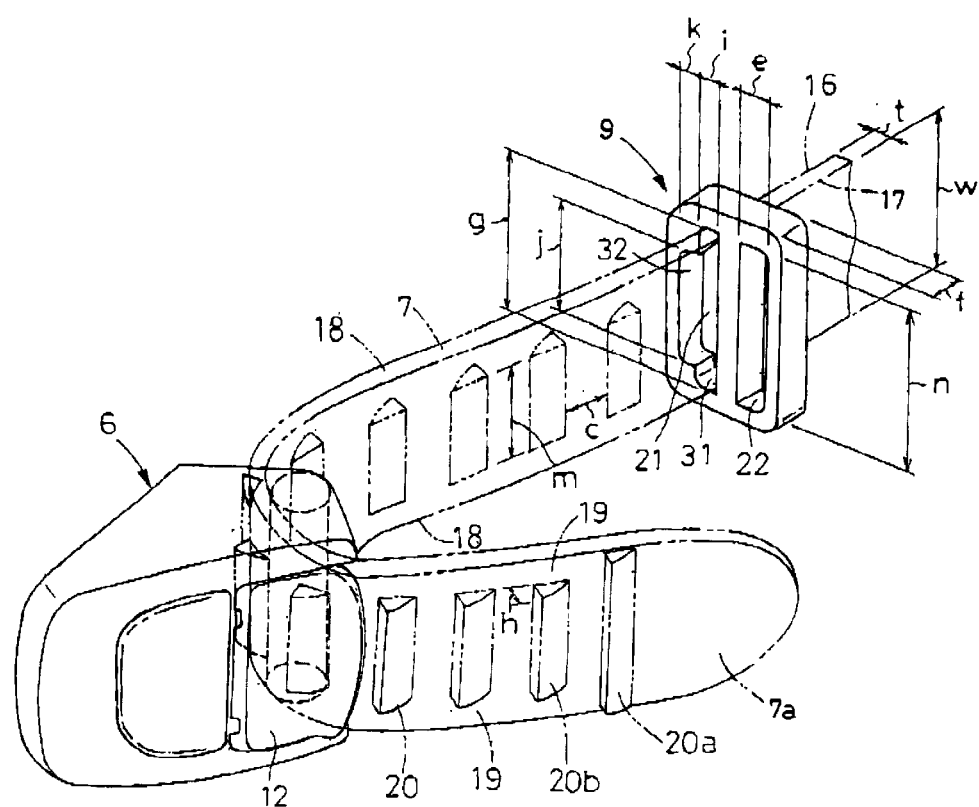
FIG. 3 is a perspective view of a band guide.

FIG. 3 is a perspective view showing the band guide 9 together with the buckle 6 indicated by solid lines and the end portion 7 of the headband 8 indicated by imaginary lines. In the band guide 9, each of the first and second guide openings 21, 22 has a width corresponding to that of the headband 8 and a height corresponding to the thickness of the headband 8. The first guide opening 21 of the band guide 9 is defined by a first guide area 31 adapted to guide transversely opposite lateral zones 19 extending along its respective side edges 18 of the belt-shaped end portion 7 and a second guide area 32 allowing the engagement teeth 20 formed on the end portion 7 to pass through this area 32. The first guide area 31 has a width g extending in the transverse direction of the end portion 7 and a height i extending in the thickness direction of the end portion 7. These width g and the height i are dimensioned so that the lateral zones 19 extending along the respective side edges 18 of the end portion 7 may be slidably moved as the end portion 7 is moved in the back-and-forth direction. In other words, these width g and the height i are dimensioned so that the width g and the height i may correspond to or slightly larger than the width w and the thickness t of the end portion 7, respectively. The second guide area 32 has a width j and a height k which are respectively dimensioned to be larger than a width m and the height h of the individual engagement tooth 20 so that the engagement tooth 20 may freely pass this guide area 32. The second guide opening 22 has a width n same as the width g of the first guide area 31 of the engagement teeth 20, the engagement tooth 20a lying most close to the pointed distal end 7a of the end portion 7 has a width m dimensioned to be substantially same as or slightly smaller than the width w of the end portion 7 so as to prevent the band guide 9 from falling off from the end portion 7. The other engagement teeth 20 have that preferably dimensioned to be smaller than that of the engagement tooth 20a. While the buckle 6 including the arm 12 is illustrated to be arranged so that this buckle 6 can be separably connected to the lens frame 2, details of the structure for such detachable attachment will be not described herein since such structure may be well-known.

In operation of the face mask 1 constructed as has been described above, the end portion 7 of the headband 8 made of a flexible elastic material may be slidably guided through the first guide area 31 of the band guide 9 to ensure that the end portion 7 can be smoothly moved in the back-and-forth direction without being twisted and/or crooked for peripheral length adjustment of the headband 8. In addition, the pointed distal end 7a of the end portion 7 well fits to the inner side of the second guide opening 22 without inconveniently bounding about within the opening 22. Thus the shape of the pointed distal end 7a is stabilized and the preventive effect against twisting and/or crooking of the end portion 7 is further improved.

In the face mask according to this inventions the end portions of the headband are guided by the respective band guides so that these end portions may slidably fit to the respective band guides in spite of the fact that the headband is made of a flexible elastic material. Thus the headband can be smoothly moved in the back-and-forth direction without being twisted and/or crooked.

What is claimed is:

1. A face mask comprising a lens frame, buckles mounted on transversely opposite extremities of said lens frame, a headband having longitudinally opposite end portions respectively turning around said buckles so that a peripheral length of the headband is adjusted, and band guides carried by said headband so as to guide said headband passing therethrough, said face mask further comprises:

said headband made of a flexible elastic plastic and said longitudinally opposite end portions thereof respectively having transversely opposite side edges extending in parallel to a longitudinal direction of said headband, a width of said headband between said side edges as well as a thickness of said headband measured along said side edges being substantially uniform, said end portions being formed on transversely middle zones of respective inner surfaces thereof destined to come in contact with a mask wearer's head with a plurality of engagement teeth arranged intermittently in a longitudinal direction of said end portions each projecting from one of said inner surfaces and having a front surface gently sloping toward a pointed distal end of one of said end portions in said longitudinal direction and a rear surface abruptly sloping in an opposite direction;

each of said buckles acts upon any one of said engagement teeth under a spring-biasing effect to enable the peripheral length of the headband to be adjusted; and each of said band guides having a first guide opening through which one of said end portions is guided from a backside toward a front of said face mask and a second guide opening through which said end portion is guided from said front toward said backside of said face mask after said end portion has been turned around one of said buckles wherein both said first guide opening and said second guide opening have a width corresponding to a width of said headband and a height corresponding to a thickness of said headband, said first guide opening being formed with a first guide area adapted to guide transversely opposite lateral zones of said end portion extending along its respective side edges and a second guide area being contiguous to said first guide area, said first guide area having a width and a height dimensioned to allow said lateral zones extending along said side edges of said end portion to be slidably moved as said end portion is moved in a back-and-forth direction of said face mask, said second guide area having a width and a height respectively dimensioned to be larger than a width and a height of said engagement teeth so that said engagement teeth freely pass said second guide area, and said second guide opening has a height substantially same as or slightly larger than said thickness of said end portion and smaller than a sum of said thickness of said end portion and said height of said engagement teeth so as to prevent said end portion passing therethrough from unintentionally moving and simultaneously to prevent said end portion from coming off from the associated one of said engagement teeth.

2. The face mask according to claim 1, wherein a plurality of said engagement teeth are provided substantially at a regular spacing in said longitudinal direction of said headband and a dimension of said second guide opening in said longitudinal direction corresponds to said regular spacing.

* * * * *